US00PP27511P3

(12) United States Plant Patent
Bernuetz et al.

(10) Patent No.: US PP27,511 P3
(45) Date of Patent: Dec. 27, 2016

(54) ***SCAEVOLA* PLANT NAMED 'BONSCA 1203'**

(50) Latin Name: *Scaevola aemula*
Varietal Denomination: Bonsca 1203

(71) Applicants: Andrew Bernuetz, Silverdale (AU); Mirza Mohammed Shoaib, North Parramata (AU)

(72) Inventors: Andrew Bernuetz, Silverdale (AU); Mirza Mohammed Shoaib, North Parramata (AU)

(73) Assignee: Bonza Botanicals PTY. LTD., Yellow Rock, NSW (AU)

( * ) Notice: Subject to any disclaimer, the term of this patent is extended or adjusted under 35 U.S.C. 154(b) by 67 days.

(21) Appl. No.: 14/545,187

(22) Filed: Apr. 4, 2015

(65) Prior Publication Data

US 2016/0295787 P1 Oct. 6, 2016

(51) Int. Cl.
*A01H 5/02* (2006.01)

(52) U.S. Cl.
USPC ..... Plt./363

(58) Field of Classification Search
USPC ..... Plt./363
See application file for complete search history.

*Primary Examiner* — Susan McCormick Ewoldt
(74) *Attorney, Agent, or Firm* — C. A. Whealy

(57) ABSTRACT

A new and distinct cultivar of *Scaevola* plant named 'Bonsca 1203', characterized by its compact, mounding to trailing plant habit; freely branching habit; early and freely flowering habit; long flowering period; pink-colored flowers; and good container and garden performance.

1 Drawing Sheet

Botanical designation: *Scaevola aemula.*
Cultivar denomination: 'BONSCA 1203'.

BACKGROUND OF THE INVENTION

The present invention relates to a new and distinct cultivar of *Scaevola* plant, botanically known as *Scaevola aemula* and hereinafter referred to by the name 'Bonsca 1203'.

The new *Scaevola* plant a product of a planned breeding program conducted by the Inventors in Yellow Rock, New South Wales, Australia. The objective of the breeding program is to create new compact, mounding and early-flowering *Scaevola* plants with numerous attractive flowers.

The new *Scaevola* plant originated from an open-pollination in Yellow Rock, New South Wales, Australia in February, 2011 of a proprietary selection of *Scaevola aemula* identified by the code number 11-26, not patented, as the female, or seed, parent with an unknown proprietary selection of *Scaevola aemula*, as the male, or pollen, parent. The new *Scaevola* plant was discovered and selected by the Inventors as a single flowering plant from within the progeny of the stated open-pollination in a controlled greenhouse environment in Yellow Rock, New South Wales, Australia in December, 2011.

Asexual reproduction of the new *Scaevola* plant by vegetative tip cuttings in a controlled greenhouse environment in Yellow Rock, New South Wales, Australia since December, 2011 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bonsca 1203'. These characteristics in combination distinguish 'Bonsca 1203' as a new and distinct *Scaevola* plant:

1. Compact, mounding to trailing plant habit.
2. Freely branching habit.
3. Early and freely flowering habit.
4. Long flowering period.
5. Pink-colored flowers.
6. Good container and garden performance.

Plants of the new *Scaevola* can be compared to plants of the female parent selection. Plants of the new *Scaevola* differ primarily from plants of the female parent selection in the following characteristics:

1. Plants of the new *Scaevola* are more compact than plants of the female parent selection.
2. Flower petals of plants of the new *Scaevola* are flatter than flower petals of plants of the female parent selection.
3. Flower petals of plants of the new *Scaevola* are darker pink in color than flower petals of plants of the female parent selection.

Plants of the new *Scaevola* can be compared to plants of the *Scaevola aemula* 'Bomy Pinka', disclosed in U.S. Plant Pat. No. 17,943. In side-by-side comparisons, plants of the new *Scaevola* differed from plants of the 'Bomy Pinka' in the following characteristics:

1. Plants of the new *Scaevola* were more compact than and not as vigorous as plants of 'Bomy Pinka'.
2. Plants of the new *Scaevola* were more freely branching than plants of 'Bomy Pinka'.
3. Plants of the new *Scaevola* had shorter internodes than plants of 'Bomy Pinka'.

4. Leaves of plants of the new *Scaevola* were shorter than leaves of plants of 'Bomy Pinka'.
5. Plants of the new *Scaevola* flowered much earlier than plants of 'Bomy Pinka'.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a side perspective view of a typical flowering plant of 'Bonsca 1203' grown in a container.

The photograph at the bottom of the sheet is a close-up view of a typical flowering plant of 'Bonsca 1203'.

DETAILED BOTANICAL DESCRIPTION

The aforementioned photographs and following observations, measurements and values describe plants grown during the late summer in 30-cm containers in an outdoor nursery in Higashiomi, Shiga, Japan and under cultural practices typical of commercial *Scaevola* production. During the production of the plants, day temperatures ranged from 15° C. to 30° C. and night temperatures ranged from 13° C. to 25° C. Plants were three months old when the photographs were taken and four months old when the detailed description was taken. In the following description, color references are made to The Royal Horticultural Society Colour Chart, 2007 Edition, except where general terms of ordinary dictionary significance are used.

Botanical classification: *Scaevola aemula* 'Bonsca 1203'.

Parentage:

*Female, or seed, parent*.—Proprietary selection of *Scaevola aemula* identified as code number 11-26, not patented.

*Male or pollen parent*.—Unknown proprietary selection of *Scaevola aemula*, not patented.

Propagation:

*Type*.—By vegetative tip cuttings.

*Time to initiate roots, summer*.—About ten days at temperatures about 21° C. to 25° C.

*Time to initiate roots, winter*.—About 15 days at temperatures about 18° C. to 21° C.

*Time to develop roots, summer*.—About three weeks at temperatures about 21° C. to 25° C.

*Time to develop roots, winter*.—About four weeks at temperatures about 18° C. to 21° C.

*Root description*.—Fibrous; white in color.

*Rooting habit*.—Freely branching; medium density.

Plant description:

*Plant form and growth habit*.—Compact, mounding to trailing plant habit; moderately vigorous growth habit.

*Branching habit*.—Freely branching habit with lateral branches potentially forming at every node; pinching enhances branching potential.

*Plant height*.—About 21.7 cm.

*Plant diameter* (*area of spread*).—About 81.7 cm.

Lateral branch description:

*Length*.—About 40.7 cm.

*Diameter*.—About 2.1 mm.

*Internode length*.—About 1.15 cm.

*Aspect*.—Outwardly, decumbent.

*Texture*.—Pubescent.

*Color*.—Close to 137C.

Leaf description:

*Arrangement*.—Alternate, simple; sessile.

*Length*.—About 4.5 cm.

*Width*.—About 2.2 cm.

*Shape*.—Spatulate.

*Apex*.—Acute.

*Base*.—Attenuate.

*Margin*.—Sparsely serrate.

*Texture, upper and lower surfaces*.—Pubescent; rough.

*Venation pattern*.—Pinnate, reticulate.

*Color*.—Developing leaves, upper surface: Close to 137A. Developing leaves, lower surface: Close to 137C. Fully expanded leaves, upper surface: Close to 137B; venation, close to 137A. Fully expanded leaves, lower surface: Close to 138B; venation, close to 143C.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about 248 flowers developing per plant.

*Flowering time*.—Early flowering habit, plants begin flowering after about three to four weeks after planting; long flower period, plants flower continuously from spring to late autumn in Japan.

*Flower longevity*.—Flowers typically last about a week on the plant; flowers not persistent.

*Fragrance*.—Present, pleasant.

*Flower buds*.—Length: About 1.5 cm. Diameter: About 2.7 mm. Shape: Lenticular. Color: Close to 75C; towards the apex, close o 138A.

*Flowers*.—Diameter: About 1.5 cm by 2.6 cm. Depth: About 1.2 cm. Tube length: About 1 cm. Tube diameter: About 3.4 mm.

*Petals*.—Quantity per flower: Five, fused at base. Length, beyond tube: About 1.4 cm. Width, beyond tube: About 4.1 mm. Shape: Narrowly elliptic. Apex: Cuspidate. Margin: Entire; weakly undulate. Texture, upper and lower surfaces: Smooth, glabrous. Color: When opening, upper surface: Close to 68B. When opening, lower surface: Close to 68C. Fully opened, upper surface: Close to 73B; venation, close to N77A to N77B. Fully opened, lower surface: Close to 73C; longitudinal central stripe, close to N144A. Throat: Close to NN155C and N144B. Tube: Close to 145B.

*Sepals*.—Quantity per flower: Two. Length: About 6.1 mm. Width: About 1.4 mm. Shape: Lanceolate. Apex: Acute. Base: Fused. Margin: Entire. Texture, upper and lower surfaces: Slightly pubescent. Color: When opening and fully opened, upper surface: Close to 137C. When opened and fully opened, lower surface: Close to 137D.

*Reproductive organs*.—Androecium: Stamen quantity per flower: Five. Anther size: About 1.3 mm by 0.7 mm. Anther shape: Ellipsoidal. Anther color: Close to 11B. Pollen: Scarce. Pollen color: Close to 11B. Gynoecium: Pistil quantity per flower: One. Pistil length: About 1.1 cm. Style color: Close to N77B. Stigma color: Close to 146B. Ovary color: Close to 146B.

*Seeds and fruits*.—Seed and fruit development have not been observed on plants of the new *Scaevola*.

Garden performance: Plants of the new *Scaevola* have been observed to have good garden performance and to tolerate rain, wind and temperatures ranging from about 0° C. to about 40° C.

Pathogen & pest resistance: Plants of the new *Scaevola* have not been shown to be resistant to pathogens and pests common to *Scaevola* plants.

It is claimed:

1. A new and distinct *Scaevola* plant named 'Bonsca 1203' as illustrated and described.

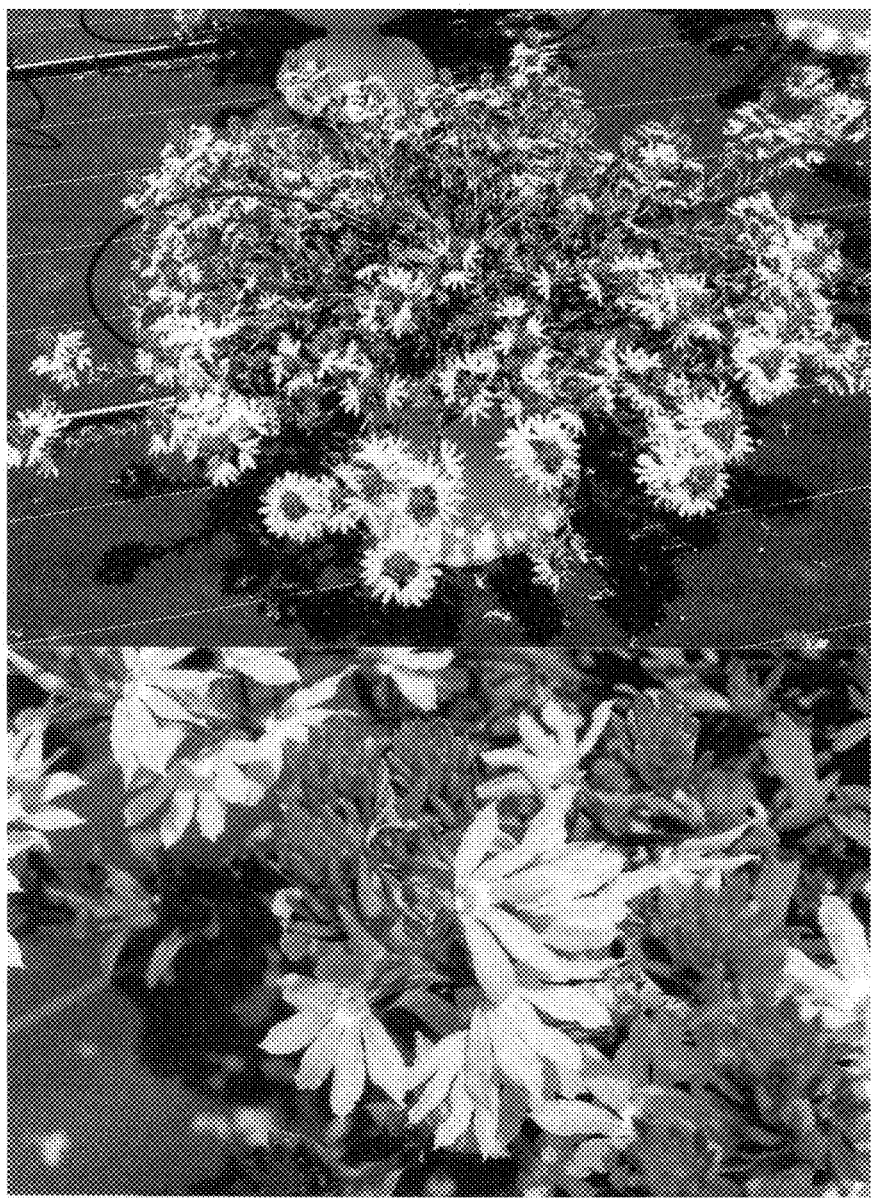

* * * * *